United States Patent [19]

Hilverda

[11] Patent Number: Plant 7,525

[45] Date of Patent: May 14, 1991

[54] CARNATION NAMED HILDANCE

[75] Inventor: Jan J. Hilverda, Aalsmeer, Netherlands

[73] Assignee: Hilverda b.v., Netherlands

[21] Appl. No.: 308,602

[22] Filed: Feb. 10, 1989

[51] Int. Cl.[5] ..... A01H 5/00

[52] U.S. Cl. ..... Plt./70

[58] Field of Search ..... Plt./70

*Primary Examiner*—James R. Feyrer

*Attorney, Agent, or Firm*—Charles W. Rummler

[57] ABSTRACT

A new spray carnation cultivar particularly distinguished by its very short and bushy growth, its continuous and prolific production of very small flowers, and the very light pink or spiraea red color of the outer two-thirds of the flower petals with more than one-half of the inner third of the petal body covered by a dark violet color. This very striking color combination provides a very dainty and distinctive blossom, suitable to be worn as a buttonhole decoration, and the plant itself has a vigorous, upright and rapid growth habit with abundant foliage providing a rather dense plant body particularly suitable for pot plant culture.

1 Drawing Sheet

BACKGROUND OF THE NEW PLANT

This new spray carnation originated as a sport of the pot carnation 'Hiltiny' (U.S. Plant Pat. No. 7,413) discovered by me in 1985 in my greenhouse at Aalsmeer, The Netherlands, this new plant being distinguished from its parent by the very much lighter pink coloration of its flowers, and I chose to propagate this sport, by means of cuttings, in the hope of producing a short, bushy pot variety suitable as a companion for the parent plant in the market place. This sport was propagated by me at my nursery in Aalsmeer with such satisfactory results that I directed that propagation of this new plant be continued through several successive generations to determine its capability of maintaining its distinctive characteristics from generation to generation and so that its homogenetic character could be assured for commercial production.

DESCRIPTION OF THE DRAWING

My new spray carnation cultivar is illustrated by the accompanying photographic drawing which shows, in full color, a flower stem bearing a number of buds in different stages of opening with at least one bud approaching a full open state, the view also showing a face view of one of the mature flowers and some of the flower petals to illustrate the color combination, the colors shown being as nearly true as it is reasonably possible to obtain by conventional photographic procedures.

DESCRIPTION OF THE NEW PLANT

The following is a detailed description of my new spray carnation cultivar based upon observations made during the current year at Aalsmeer, the color designations being according to The R.H.S. Colour Chart published by The Royal Horticultural Society of London, England.

THE PLANT

Origin: Sport.

Parentage: A pot carnation variety 'Hiltiny' (U.S. Plant Pat. No. 7,413).

Classification:

*Botanic.*—*Dianthus caryophyllus* L.

*Commercial.*—Pot Carnation.

Form: A short, erect bush having an abundant production of foliage.

Height: From about 20 to 25 cm.

Growth habit: Strong, vigorous, with a rapid growth rate.

Branching character: Alternate.

Foliage:

- *Quantity.*—Abundant.
- *Size of leaf.*—About 6 to 8 cm. in length.
- *Leaf shape.*—Elliptic with entire margins and acute tip.
- *Texture.*—Leathery.
- *Color.*—Blue Green on both upper and under sides of leaves.
- *Leaflets.*—None.
- *Ribs and veins.*—The leaves have a prominent midrib.

THE BUD

Size: Small.

- *Diameter.*—About 5 to 8 mm.
- *Length.*—Approximately 20 mm.

Form: Cylindrical.

Opening rate: About three to four days.

Color of petals:

- *When sepals first divide.*—Very Light Pink.
- *When petals begin to unfurl.*—Very Light Pink.

Sepals:

- *Number.*—Five.
- *Shape.*—Long ovate with acute tip.
- *Character.*—The sepals are hooded over the bud before dividing and stand up as the flower petals unfurl.
- *Color.*—Inside: Light Green to White. Outside: Dark Green.
- *Striae.*—None.

Calyx:

- *Shape.*—Cylindrical.
- *Size.*—Long.
- *Splitting.*—The calyx does not split.
- *Aspect.*—Smooth.

Flower stem:

*Length.*—About 20 cm.
*Character.*—Rigid and erect.
*Color.*—Dark Green.

THE FLOWER

Blooming habit: Continuous with profuse flower production.
Size of bloom: Quite small.
*Diameter.*—About 30 mm.
*Depth.*—About 10 to 12 mm.
Borne: In clusters on strong stems having longitudinally-spaced relation along the flowering stem.
Flower shape: When bloom first opens, high centered. When bloom matures, it tends to flatten.
Petalage:
*Number of petals.*—About 7 to 10.
*Arrangement.*—Imbricated.
*Form.*—Fan-shaped with dentated margins and a rounded end.
*Texture.*—Soft.
*Appearance.*—Velvety.
*Color.*—All petals, Spiraea Red, RHS 63D, with a relatively large Violet, RHS 83-A, area somewhat below the center of the petal body.
Flower stem:
*Length.*—About 20 cm.
*Color.*—Dark Green.
*Character.*—Sturdy and upright.
Discoloration after full bloom: None.
Persistence: The flowers hang on and dry.
Fragrance: Weak.
Lasting quality: About 14 to 21 days on the plant.

REPRODUCTIVE ORGANS

Stamens:
*Number.*—Six to eight.
*Arrangement.*—Evenly arranged around the ovary.
*Anthers.*—Size: Small. Color: Cream White.
*Filaments.*—Length: About 10 to 12 mm. Color: White.
*Pollen.*—Color: White.
Pistils:
*Number.*—One.
*Style.*—Length: About 20 to 25 mm. Color: White.
*Stigma.*—Color: White.
Character of ovaries: Normal.

THE FRUIT

Fertility: The fruit is fertile.
Shape: Lozenge-shaped.
Color at maturity: Yellow/Brown.

This carnation cultivar most nearly resembles its parent 'Hiltiny' and distinguishes from its parent by having a much lighter color of spiraea red as compared with the magnolia purple of its parent.

I claim:

1. The new and distinct pot carnation, substantially as herein shown and described, characterized by its very small flowers of a very light pink color particularly distinguished by the flower petals having a dark violet area near the base and the plant being of short height with abundant, rather dense production of foliage.

* * * * *

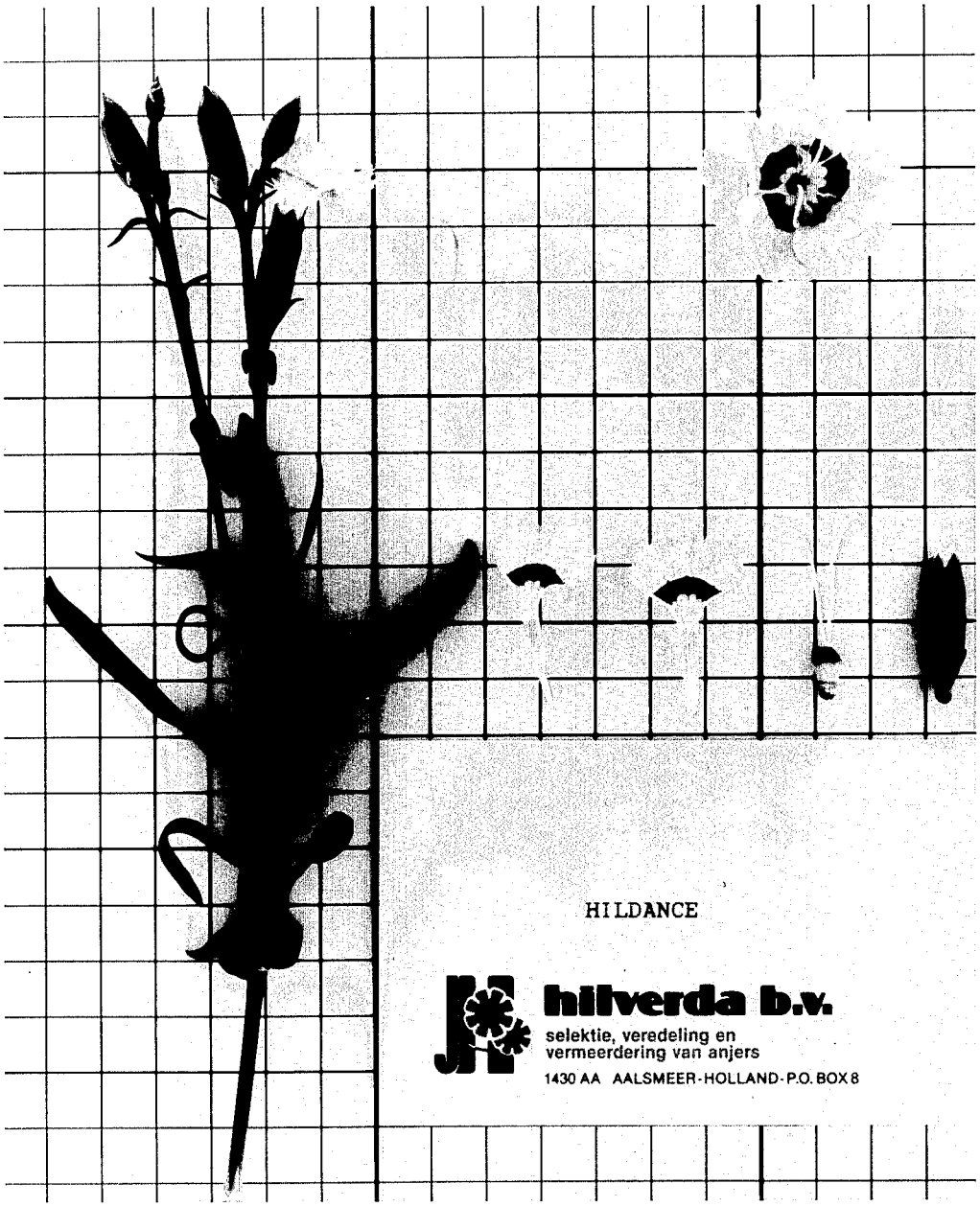
HILDANCE
hilverda b.v.
selektie, veredeling en
vermeerdering van anjers
1430 AA AALSMEER-HOLLAND-P.O. BOX 8